(12) United States Patent
Lou

(10) Patent No.: US 9,993,180 B2
(45) Date of Patent: Jun. 12, 2018

(54) ALERT DEVICES AND APPARATUS

(71) Applicant: Windrider R.S.B Aviation Limited, Kowloon, Hong Kong (CN)

(72) Inventor: Tsz Ming Lou, Hong Kong (CN)

(73) Assignee: WINDRIDER R.S.B AVIATION LIMITED, Kowloon, Hong Kong (CN)

( * ) Notice: Subject to any disclaimer, the term of this patent is extended or adjusted under 35 U.S.C. 154(b) by 0 days. days.

(21) Appl. No.: 15/636,809

(22) Filed: Jun. 29, 2017

(65) Prior Publication Data
US 2018/0000384 A1  Jan. 4, 2018

(30) Foreign Application Priority Data

Jul. 4, 2016  (HK) ................................ 16107751.6

(51) Int. Cl.
| | | |
|---|---|---|
| G08B 23/00 | (2006.01) | |
| A61B 5/11 | (2006.01) | |
| G08B 21/02 | (2006.01) | |
| A61B 5/00 | (2006.01) | |
| G06F 1/16 | (2006.01) | |

(52) U.S. Cl.
CPC .......... *A61B 5/1116* (2013.01); *A61B 5/1114* (2013.01); *A61B 5/6828* (2013.01); *G06F 1/163* (2013.01); *G08B 21/02* (2013.01)

(58) Field of Classification Search
CPC ... A61B 5/1116; A61B 5/1114; A61B 5/6828; G06F 1/163; G08B 21/02
USPC ....................................................... 340/573.1
See application file for complete search history.

(56) References Cited

U.S. PATENT DOCUMENTS

| | | | |
|---|---|---|---|
| 7,771,318 B2 | 8/2010 | Narayanaswami | |
| 2009/0135133 A1* | 5/2009 | Kunzler | ................ A63F 13/06 345/156 |
| 2014/0145848 A1* | 5/2014 | Amir | .................... G08B 21/043 340/573.1 |
| 2016/0242986 A1* | 8/2016 | Nagata | ....................... A61F 5/01 |
| 2017/0092094 A1* | 3/2017 | Yang | .................. G08B 21/0415 |

FOREIGN PATENT DOCUMENTS

| | | |
|---|---|---|
| CN | 104900019 A | 9/2015 |
| CN | 105389960 A | 3/2016 |
| CN | 205334699 U | 6/2016 |

* cited by examiner

*Primary Examiner* — Kerri McNally
(74) *Attorney, Agent, or Firm* — Nixon Peabody LLP; Jeffrey L. Costellia (57) ABSTRACT

A cross-leg alert device comprising a cross-leg detector for detecting a cross-legged posture and an alert generator is disclosed. The alert generator is to generate an alert to a user upon the cross-leg detector detecting a change in posture from a non-cross-legged posture to a cross-legged posture. The cross-leg detector is for detecting a cross-legged posture and the alert generator is for generating an alert signal to a user when the cross-leg detector has detected a change in posture from a non-cross-legged posture to a cross-legged posture.

19 Claims, 6 Drawing Sheets

ALERT DEVICES AND APPARATUS

FIELD

The present disclosure relates to alert devices apparatus, and more particularly to alert devices for generating an alert signal to alert or remind a user to change or correct body posture such as sitting postures.

BACKGROUND

Good body posture is important to maintain good body health and can help prevent many healthy issues. For example, it has been suggested that prolonged crossed legs while seated may cause back and neck pain in the long term, since sitting with legs crossed puts hips in a torqued position, which can lead to the rotation of one of the pelvic bones. Since the pelvis is the base of support for your spine, it puts unnecessary pressure on the neck and lower and middle back when it's rotated and unstable. The longer a person sits with legs crossed, the more pressure is put on the spine, which increases the odds an issue is developed. Other known problems associated with cross-legged sitting and other improper body postures include vein damages, blood pressure increase, temporary paralysis and long-term numbness.

Therefore, it would be useful and beneficial to provide means to help maintain a good body posture, for example a good sitting posture.

DISCLOSURE

An alert device for wearing on a thigh of a user is disclosed. The alert device comprises an alert generator which comprises an alert signal generation device for generating a user perceivable alert signal when the user is in a crossed leg sitting posture when both thighs of the user are in abutment contact with the alert device and with the alert device between both thighs.

The alert signal may be in the form of an applied pressure, the applied pressure being at a harmless level which is sufficient to cause perception or notice of the user; a non-harmful and user perceivable electric shock or pulse; or an audible sound.

The alert generator may comprise a pressure applicator which is arranged to generate a harmless but perceivable or noticeable pressure on thigh skin of the user or pain during alert operations; an electric shock generator which is arranged to generate a harmless but noticeable electric shock or shock pulses to the user during alert operations; or an audible generator which is arranged to generate an audible alarm to the user during alert operations.

The alert device may further comprise a second thigh detector, wherein the second thigh detector is to function as an incoming thigh detector for detecting an incoming thigh and comprises a second thigh detection surface, and the second thigh detection surface is movable between a detection state or standby state when no alert signal is generated to the user by the alert generator and an activation state when the alert signal is generated to the user by the alert generator; and wherein the second thigh detection surface is arranged to trigger, activate or operate the alert generator to generate the alert signal when crossed leg sitting of the user is detected by the second thigh detector.

The alert device comprises a base portion which is in abutment contact with a wearing thigh of a user when the alert device is worn on the wearing thigh and defines a thigh contact surface, and wherein the second thigh detector or the second thigh detection surface is axially elevated or offset from the base portion by a resiliently deformable support structure and is to move in an axial direction to change its axial levels when moving between the standby or detection state and the activation state.

The second thigh detection surface, the support structure and the base portion may cooperate to define a resiliently deformable hollow structure and the hollow structure defines a hollow internal compartment, and wherein the alert generator is inside the hollow internal compartment at least when in the standby or detection state.

The second thigh detection surface, the support structure and the base portion may be integrally formed from a semi-rigid, resilient and mouldable material.

The second thigh detector may comprise a central portion and the second thigh detection surface faces away from the base portion, and an under-surface which is on opposite side of and is opposite facing to the second thigh detection surface, and wherein the alert generator comprising a stud member which is suspended from the central portion and extends towards the base aperture in the axial direction.

The central portion and the base portion may share a common central axis, the common axis being orthogonal to both the central portion and the base portion.

The support structure may comprise a plurality of spaced part stays and an inter-stay aperture is defined between adjacent stays, and wherein the stays extend radially from the central portion and curves concavely to join the base portion to form a dome-shaped hollow support structure when in the standby or detection state.

The dome-shaped hollow support structure may become a double arched shaped hollow support structure when changed from the standby or detection state to the activation state.

The alert device may comprise a resilient biasing device which is arranged to bias the second thigh detection surface in the standby or detection state and to provide an urging force to return the thigh detection surface to the standby or detection state when in the activation state.

The alert device may be for wearing on a stationary thigh and the second thigh detection surface is an incoming thigh detection surface for detecting an incoming thigh which moves towards abutment contact with the stationary thigh to form a crossed leg sitting posture; or wherein the alert device is for wearing on a moving thigh and the second thigh detection surface is stationary thigh detection surface for detecting a stationary thigh which is in abutment contact with the moving thigh to form a crossed leg sitting posture.

The alert generator may comprise electrical or electronic circuitry to generate audible or skin sensible or perceivable alert signals and a switch operable to actuate the electrical or electronic circuitry to generate the audible or skin sensible or perceivable alert signals.

The switch may be operable between an actuation state to actuate the electrical or electronic circuitry to generate an alert signal and a standby state when the electrical or electronic circuitry does not generate an alert signal; and wherein the thigh detection surface forms part of the switch so that movement of the thigh detection surface from the standby or detection position to the actuation position is to move the switch from the standby or detection state to the actuation state.

A cross-leg alert apparatus comprising an alert device as described herein and an attachment means for attaching the alert device to a first thigh of a user.

The attachment means may be a resilient or elastic band and the alert device is mounted on the resilient or elastic band; or wherein the attachment means comprises a self-adhesive device integrally formed on the base portion of the alert device.

The cross-leg alert apparatus may comprise a plurality of alert devices according to any preceding claims, wherein the alert devices are distributed along length of the apparatus.

A cross-leg alert apparatus comprising a cross-leg detector for detecting a cross-legged posture and an alert generator is also disclosed. The alert generator is to generate an alert to a user upon the cross-leg detector detecting a change in posture from a non-cross-legged posture to a cross-legged posture. The alert is set to be a non-invasive alert which is at a level sufficient to cause physical stress or discomfort to a user without harm so that a wear upon reception of the alert will realize improper sitting posture and reposition his/her leg.

The cross-leg detector is for detecting a cross-legged posture and the alert generator is for generating an alert signal to a user when the cross-leg detector has detected a change in posture from a non-cross-legged posture to a cross-legged posture.

In some embodiments, the alert generator is to generate a non-invasive alert signal.

In some embodiments, the alert device and/or the alert generator is weight actuated.

In use, the alert device is worn on the thigh of a user for detection of contact abutment with an approaching thigh. When cross legged sitting occurs, compressive force following contact abutment between an approaching thigh and the worn alert device will operate the alert device to generate an alert to the wearer. The wearer can in response to the alert elect or decide whether to resume a non-cross-legged position or to remain in the cross-legged position.

A cross-leg alert that formed as one integral part is also disclosed. The cross-leg alert device comprises a cross-leg detection surface which is movable from an initial position corresponding to a non-cross legged posture, to an actuation position corresponding to a cross-legged posture, and which is to move from the initial position to the actuation position when the posture of the wearer changes from the non-cross-legged posture to the cross-legged posture, and wherein the alert generator comprises a pressure applicator projecting from when the cross-leg detection surface or projects from a surface which is on opposite side of the cross-leg detection surface.

The cross-leg alert device is light weight, low-cost and fast to manufacture. The cross-leg alert device is particularly useful for providing immediate alert to user, such that the user is aware of crossing the legs and changes the posture accordingly.

FIGURES

The present disclosure will be described by way of example and with reference to the accompanying figures, in which:

FIGS. 3B and 3C are schematic views depicting the user of FIG. 3A when sitting with legs crossed, FIG. 3B1 is an enlarged view of the dotted portion of FIG. 3B, FIG. 6A1 is a schematic view depicting an example use of the example cross-leg alert device when worn on the thigh of a user, FIGS. 6B1 and 6B2 are schematic views depicting the user of FIG. 6A when sitting with legs crossed, FIGS. 7A1 and 7A2 are schematic views of one other example cross-leg alert device on the right and left legs respectively, FIG. 7B is a schematic view depicting the user of FIGS. 7A1 and 7A2 when sitting with legs crossed.

DESCRIPTION

Figure 1:
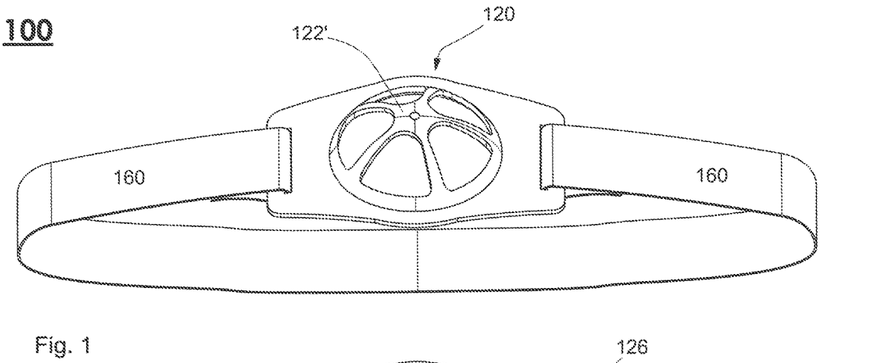
FIG. 1 is a perspective view of an example cross-leg alert device according to the present disclosure.

An example body posture alert apparatus 100 depicted in FIG. 1 comprises an alert device 120 and an attachment means 160. The alert device 120 comprises an improper or poor posture detector and an alert generator 140 is depicted in FIGS. 1 and 2A to 2D. The example body posture alert apparatus 100 in this example is configured and usable as a crossed leg alert apparatus, as depicted in FIGS. 3A, 3B, 3B1 and 3C. The example alert device 120 comprises a crossed leg detector and an alert generator 140 and is mounted on a thigh attachment device 160. The alert device 120 comprises a main body which is a hollow body comprising a base portion 260 and an elevated portion. The elevated portion is supported on the base portion and comprises a first surface 122, a second surface 124, and a peripheral surface interconnecting the first surface and the second surface. The second surface and the first surface are opposite facing and are on opposite facing sides of the elevated portion. The first surface first surface is facing away from the base portion 160 and is to function as an incoming-thigh detector and defines an incoming-thigh detection surface. The incoming-thigh detection surface 122 is also referred to as a thigh sensing surface or an incoming-thigh sensing surface herein.

The incoming-thigh detection surface 122 is elevated from the base portion 126 and is configured to face away from the thigh surface of a user on which the alert device 120 is worn. The second surface 124 is elevated from the base portion 126 and is configured to face towards the thigh surface of a user when the alert device is worn on the user's thigh. The base portion 126 is configured to seat on the thigh surface of a user when the alert device is worn on the user's thigh and will be in abutment contact with the thigh surface of a user when so worn.

Figure 2A:
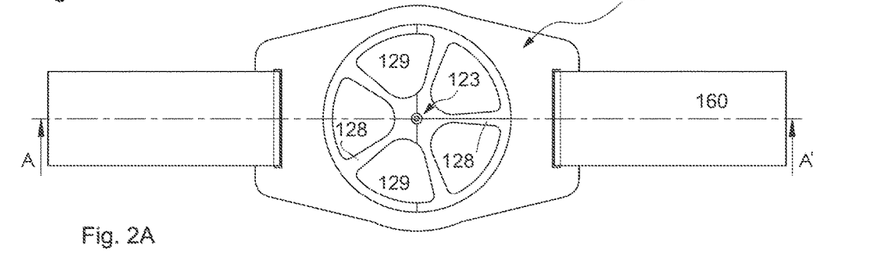
FIG. 2A is a top plan view of the example device of FIG. 1.

The main body comprises a central portion 123 which is elevated from the base portion 126 by a plurality of stays 128. The central portion 123, the stays 128 and the base portion 126 cooperate to define a hollow internal compartment of the main body. The base portion 126 defines a central aperture or a base aperture 130 which is an entry aperture to the hollow compartment. The central portion 123 defines a main thigh sensing surface 122' which is facing away from the base aperture 130 and supported by the plurality of stays 128. The stays 128 are radial extending and extend radially outwards from the central portion 123 and terminate at the base portion 126. The base portion 126 extends continuously to surround the base aperture and form a closed circuit. The lower ends of the stays 128 join the base portion 126 and the closed circuit provides structural support to maintain the stays 128 in the elevated state unless deformed by an external applied force. The stays 128 are spaced apart and an aperture 129 is defined between a pair of adjacent stays 128. In some embodiments as that of FIG. 1, a fan shaped or circular-sector shaped is defined between a pair of adjacent stays 128, as depicted in FIG. 2. Each of the stays 128 curves towards the base portion 126 as it extends radially outwards from the central portion 123. The central portion 123 and the stays 128 cooperate to define a hollow main body having a dome-shaped top. The plurality of stays 128 and the central portion 123 cooperate to define a hollow thigh sensing assembly. The hollow thigh sensing assembly is elevated from the base portion.

The example thigh sensing assembly comprises a dome shaped or partially spherical shaped cage structure or cage assembly. The cage structure or the cage assembly is substantially hollow and defines a hollow compartment which is communicable with outside of the main body through the inter-stay apertures 129. The hollow cage structure or the cage assembly defines a well-ventilated thigh sensing assembly for enhanced user comfort. The hollow compartment of the main body has a dome-shaped or partial spherical-shaped ceiling. The curved stays 128 and the main sensing surface 122' cooperate to define a dome shaped or partially spherical shaped internal space or compartment. The lower axial end or bottom of the thigh sensing assembly connects with the base portion 126 and the base portion 126 defines the main aperture 130 into the hollow internal space or compartment of the sensing assembly.

The thigh sensing assembly is configured such that when the incoming thigh sensing surface 122, more particularly the main thigh sensing surface 122', is subject to an applied force which acts to push the main thigh sensing surface 122', more particularly the main thigh sensing surface, towards the direction of the base aperture 130, the thigh sensing assembly will be deformed such that the main thigh sensing surface 122' is depressed and moves towards the base aperture 130. When this deformation occurs, the main thigh sensing surface 122' would move into the space which was part of the hollow compartment before deformation occurs. The plurality of stays defines a resiliently deformable network, or more particularly, resiliently deformable network, which functions to support the incoming thigh sensing surface 122', more particularly the main thigh sensing surface 122', in the neutral, un-deformed, state of the alert device. The resiliently deformable network also functions to resiliently restore the alert device to its un-deformed neutral state when the applied forced is removed. When deformation occurs, movement of the main thigh sensing surface 122' or the main thigh sensing surface 122' towards the base aperture 130 will at the same time bring along deformation of the stay assembly. As depicted in FIGS. 2C and 2D, the underside or the second surface 124 of the thigh sensing surface 122' has a concave shape along the longitudinal direction of the alert device 100 as defined by the longitudinal axis A-A'. The concave curvature of the concaved shaped underside 124 gradually increases as the thigh sensing surface 122' or the main thigh sensing surface 122' gradually moves towards the base aperture 130. When the main thigh sensing surface 122' reaches a same axial level as the base portion, a double concave curvature is formed on the underside 124 of the main body, as depicted in FIG. 2D. In typical example operations when the alert device is worn on the thigh of a user, the applied force is due to the weight of an incoming thigh of a user when the user moves the incoming thigh into a crossed leg posture.

The main thigh sensing surface 122' is elevated above the base portion 126 by the plurality of stays 128. When the alert device is worn on the thigh of a user, the hollow thigh sensing assembly becomes a protruding structure which protrudes from the thigh surface. In some embodiments as that of FIG. 1, the main thigh sensing surface 122' is at top, preferably the top center, of the dome shaped thigh sensing assembly or partially spherical shaped thigh sensing assembly. The stays 128 are resilient stays made of semi-rigid and resilient materials such as soft plastics, semi-rigid plastics or silicone rubber so that the thigh sensing assembly is resiliently deformable when another thigh of the wearer not wearing the alert device comes into abutment contact with the thigh sensing assembly as a result of leg crossing. In some embodiments, soft yet strongly resilient materials such as aluminum or aluminum alloys may be used. In some embodiments such as the present, the incoming thigh sensing sub-assembly comprising the plurality of stays 128 and the main thigh sensing surface 122' are integrally moulded as a single piece. A singly moulded sub-assembly has less or no joints and mitigates the risks of injuries due to sharp joints or broken joints and enhances user safety. In some embodiments such as that of FIG. 1, the thigh sensing assembly is resiliently deformable in an axial direction of the dome shaped assembly, this axial direction being along the dome axis which passes though the center axis of circles defining the dome. In some embodiments such as the present, the axial direction passes through the center of the main sensing surface 122'. When an axial compressive force is applied downwardly on the main thigh sensing surface 122', the dome shaped sensing assembly will be deformed and moves towards the main aperture 130, as depicted in FIG. 2D. The resiliently deformed sensing assembly will return to its un-deformed state of FIGS. 2A, 2B and 2C by inherent spring resiliency of the stays 128 when the downward compressive force acting on the thigh sensing assembly is removed.

In some embodiments such as the present, the stays are of equal length. In other embodiments, the stays are of unequal length.

In some embodiments such as the present, the angular spacing between adjacent stays is substantially identical or uniform. In other embodiments, the angular spacing between adjacent stays is not substantially identical or is non-uniform.

In the example embodiment of FIG. 1, there are five stays which are distributed in a star shaped configuration and the angular spacing between adjacent stays is about 70 or 72 degrees. Where there are more stays, for example, six to eight stays or more, the angular spacing will be smaller and where there are less stays, example, two to four stays, the angular spacing will be higher without loss of generality. In general, a plurality of three to six equally spaced stays would be beneficial and adequate.

The example alert device includes a stud member 142 which is to function as an alert generator 140. The stud member 142 includes an elongate body 142 which is dependent from the central portion 123. More specifically, the elongate body 142 projects from the second surface 124 of the main body and extends towards the base aperture 130. The elongate body 142 extends along a longitudinal axis which is at an angle to the main thigh sensing surface 122' or the central portion 123. In some embodiments such as the present, the longitudinal axis of the elongate body 142 is substantially orthogonal to the central portion 123. In some example, the stud member 142 may be in the form of a rounded boss. In some embodiments, the stud member gradually tapers as it extends towards the base aperture 130 to concentrate force collected at the thigh sensing surface to produce a more noticeable alert on the wearer. The extent of tapering may be varied to adjust the level of physical alert required to be applied. For example, a stud member having a smaller free end will produce a larger stimulating pressure on the wearer and a stud member having a larger or wider free end will produce a larger stimulating pressure on the wearer.

In some embodiments such as the present, the elongate body has a central longitudinal axis which is coaxial or aligned with the central axis of the central portion 123 and projects in the axial direction away from the main thigh sensing surface 122' and extends towards the base aperture 130. In some embodiments such as the present, the stud member 142 has a rounded free end to mitigate potential harm or injuries to a wearer to provide a non-invasive alert. In some embodiments, the free end of the stud member may be rugged or cornered to provide a higher level of non-invasive alert sensation to a user.

The protruding stud member 142 projects from the second surface 124 or an underside of the main body and extends towards the base aperture 130. When the thigh sensing surface 122' is subject to a compressive force acting in the direction of the base aperture 130 due for example to thigh crossing when in use, the stud member 142 will in response to the applied force protrude beyond the base aperture 130 and act on the skin of the wearer to apply a noticeable alert pressure on the thigh of the wearer. In some embodiments such as the present, the noticeable alert pressure will cause a noticeable and non-harmful pain to a user.

Figure 3A:
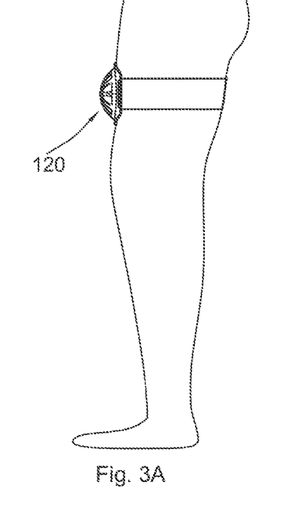
FIG. 3A is a schematic view depicting an example use of the example cross-leg alert device when worn on the thigh of a user.
Figure 3B:
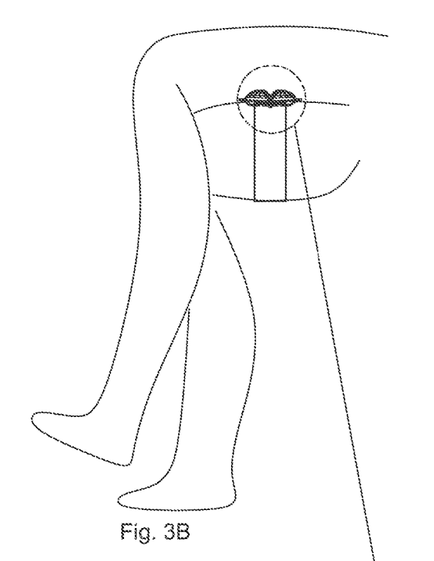
Figures 3B, 3C:
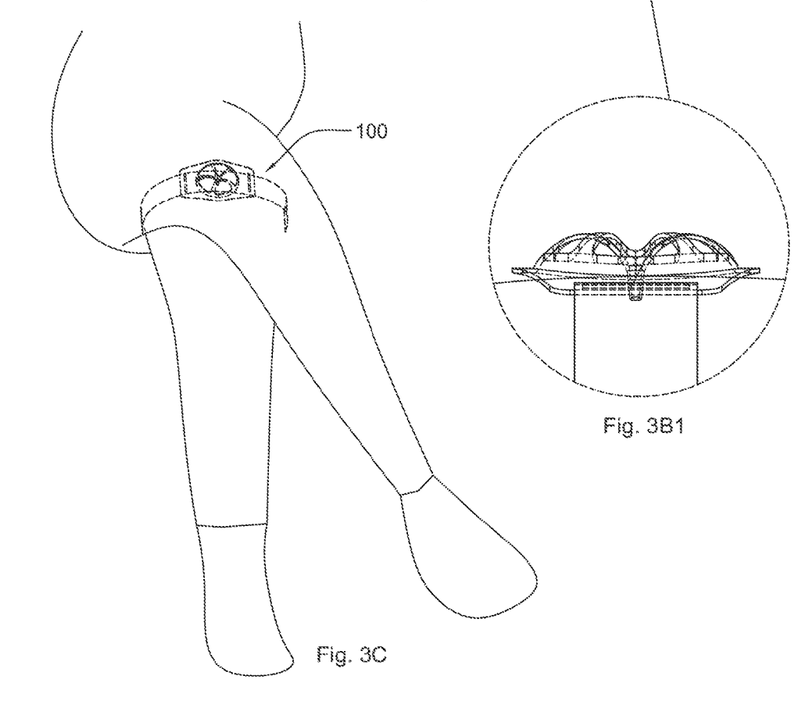

The example protruding member 142 is to generate an alert signal to a user when crossed leg sitting of the user occurs and is detected. The thigh sensing surface 122' of the present embodiment is arranged to detect crossed leg sitting so that a physical alert signal will be generated when crossed leg sitting of a user occurs. The physical alert signal in the present example is in the form of an applied pressure which is sufficient to cause a non-harmful awakening pain to a wearer. In some embodiments, the alert signal may be in the form of electric signals or audio signals. To facilitate crossed leg detection, the alert device may be worn on the thigh of a user with the main thigh sensing surface 122' facing away from the wearing thigh, as depicted in FIGS. 3A-3C.

The axial length of the protruding member 142 is arranged such that the free end of the protruding stud member will move from a non-protruding position to a protruding configuration. When in the protruding configuration, the free axial free end protrudes beyond or below the base portion 126 and encounters and presses on the thigh surface of a user when cross-leg sitting of the user occurs. The rigidity, length and shape of the free end of the stud member 142 is configured to cause discomfort or even a small, non-harmful, pain to the wearing user to alert the wearing user to change or correct the sitting posture. The user will usually change the sitting posture in response upon the immediate sensation of pain or discomfort generated by the protruding stud member 142.

In some embodiments, the protruding member 142 is pin-shaped, shaft-shaped or column-shaped and may be made of rigid materials such as hard plastics, metal or wood or semi-rigid and resilient materials such as silicone rubber or semi-rigid plastics. In order to generate alert without causing excessive pain or harm to a user, semi-rigid materials are preferred. To adapt for application of an effective reminding alert to a user, the protruding member has a base in abutment with the ceiling of the dome-shaped sensing assembly and tapers to narrow and terminates at the free axial end which is proximal the base aperture 130. The free axial end may be flat or rounded, although a rounded end would mitigate potential harm or excessive pressure on a user.

Figure 2B:
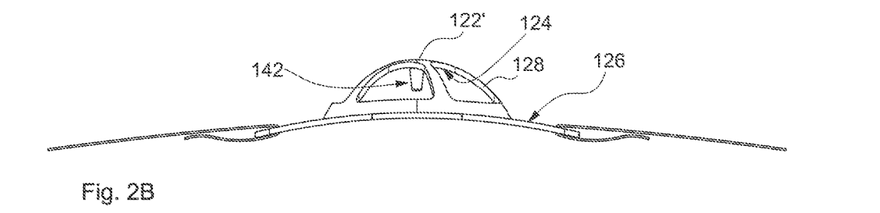
FIG. 2B is a side elevation view of the example device of FIG. 1.
Figure 2C:
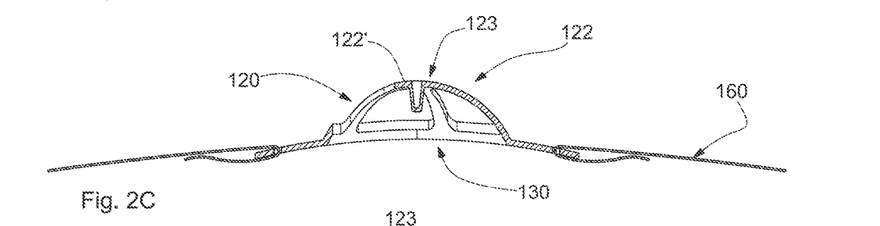
FIG. 2C is a cross-sectional view of the example device of FIG. 1 taken along a longitudinal section line A-A' which passes through a longitudinal centerline of the central portion 123 and/or the stud member.
Figure 2D:
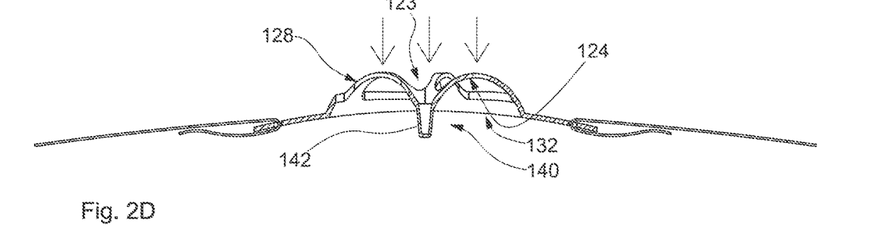
FIG. 2D is the cross-sectional view of FIG. 2C with the example device deformed in response to an axially applied compressive force.

As depicted in FIGS. 2B, 2C and 2D, the protruding stud member 142 is suspended by a stay assembly comprising the plurality of stays. The stays form a resilient stay structure which is to function as an ensemble of cantilevers, and the cantilevers are distributed to support the alert generator 140 and the protruding member 142 above the thigh surface of a user during the neutral state of FIGS. 1, 2A and 2B when worn by a user. In some embodiments such as the present, the cantilevers are curved to form a dome-shaped hollow support structure.

In some embodiments such as the present, the elongate body of the stud member 142 has an axial length which is slightly less than the clearance between the ceiling or top of the dome-shaped thigh sensing assembly and the base portion 126, so that the axial free end of the protruding stud member 142 stops short of or is slightly above the underside of the base member 126 when the sensing assembly is in the un-deformed or neutral state when the stays are un-deformed or in its fully extended state. The underside of the base member 126 is the side which is in contact with the skin of a user. In other embodiments, the free end of the stud member 142 is flush with or protrudes slightly beyond the base portion 126 without loss of generality.

The example cross-leg detector or alert device 120 is mounted on an attachment means such as an elastic wearing band 160 in order to attach to a user. The band may be a woven band, a rubber band, or a band of an appropriate materials which would retain the cross-leg detector 120 in position when worn on the thigh of a user, as depicted in FIG. 3A.

Referring to FIG. 3A, a user wears the alert apparatus 100 on a first thigh (which is a stationary thigh), with the wearing band 160 securing the cross-leg detector 120 in place and the thigh sensing surface facing forwardly and away from the first thigh. When the user changes the sitting posture to the crossed leg posture, with the second thigh (which is a moving thigh) above and in abutment contact with the first thigh, as depicted in FIGS. 3B and 3C, the rear or lower surface of the second thigh, which is the right thigh in this example, would be in abutment contact with the forward surface of the first thigh, which is the left thigh in this example. When in this crossed-leg posture, the rear surface of the right thigh will be in abutment contact with the main thigh sensing surface 122' and the weight of the second thigh will depress the main thigh sensing surface 122' and move the stud member 142 to move in the axial direction towards the base apertures 130 and the forward surface of the first thigh. In other words, depression of the main thigh sensing surface 122' in the axial direction towards the base aperture 130 will also move the protruding member 142 towards the base aperture 130 of the base portion 126. When the protruding member 142 is moved to project beyond the base portion 126 as depicted in FIG. 2D, the free end of the protruding member 142 will encounter the forward thigh surface of the user and this encounter will generate a physical alert to the user. Upon receipt of the physical alert, a user will realize that cross-legged sitting has occurred and will typically respond by restoring to a non-cross-legged sitting posture. The main thigh sensing surface 122' will return to its original, neutral or un-deformed state due to spring resiliency of the stays when the applied force is removed when a user returns to the non-crossed-leg posture.

In example applications, a user may elect to wear the alert apparatus 100 on the moving second thigh, with the thigh sensing assembly facing rearwards or facing away from the rear surface of the moving thigh, that is, the second thigh. When the user changes sitting posture to move into leg crossing, such that the second thigh is above the first thigh, the second thigh will move the thigh sensing assembly to approach the first thigh. When the second thigh moves into abutment contact with the first thigh, the weight of the second thigh, which carries the thigh sensing assembly, will move the main thigh sensing surface upwards towards the base aperture 130 to apply an alert on the moved second thigh, and the above description applies mutatis mutandis. Where a user has a different cross leg sitting posture tendency or habit, for example, with the first thigh being a moving thigh which is above the second thigh which is a stationary thigh when cross legged sat, the user may wear the alert device on the first thigh (which is the moving thigh) or the second thigh (which is the stationary thigh). When worn on the first thigh, which is the moving thigh to move into crossed-leg posture, the main thigh sensing surface 122' will be worn facing rearwards and away from the moving thigh. When the user changes sitting posture to move into leg crossing, such that the first thigh is above the second thigh, the thigh sensing assembly will follow the movement of the first thigh to approach the second thigh. When the first thigh moves into abutment contact with the second thigh, the weight of the first thigh, which carries the thigh sensing assembly, will move the main thigh sensing surface upwards towards the base aperture 130 and applies an alert on the moved first thigh, and the above description applies mutatis mutandis.

Likewise, the user may elect to wear the alert device on the second thigh (which is the stationary thigh) with the thigh sensing surface facing forwardly and away from the second thigh, and the description on and in relation to FIG. 3A is incorporated herein mutatis mutandis.

In general, the alert device may be worn on the moving thigh, the stationary thigh or both thighs. When worn on the moving thigh, the thigh sensing surface is to face rearwards of the wearing thigh. When worn on the stationary thigh, the thigh sensing surface is to face forwards of the wearing thigh.

When worn on the moving thigh or the stationary thigh, the main thigh sensing surface 122' will be subject to an applied force and will be pushed towards the base aperture 130, and the stud member will generate an alert signal when thigh crossing occurs when the user changes into the crossed-leg sitting posture.

Figure 4:
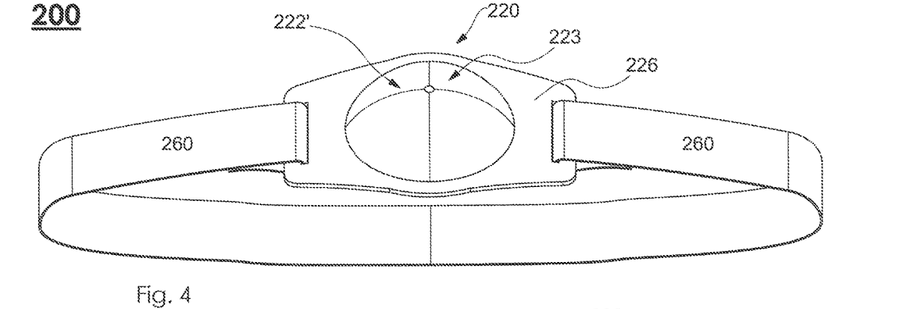
FIG. 4 is a perspective showing another example cross-leg alert device according to the present disclosure.
Figures 4A, 4B:
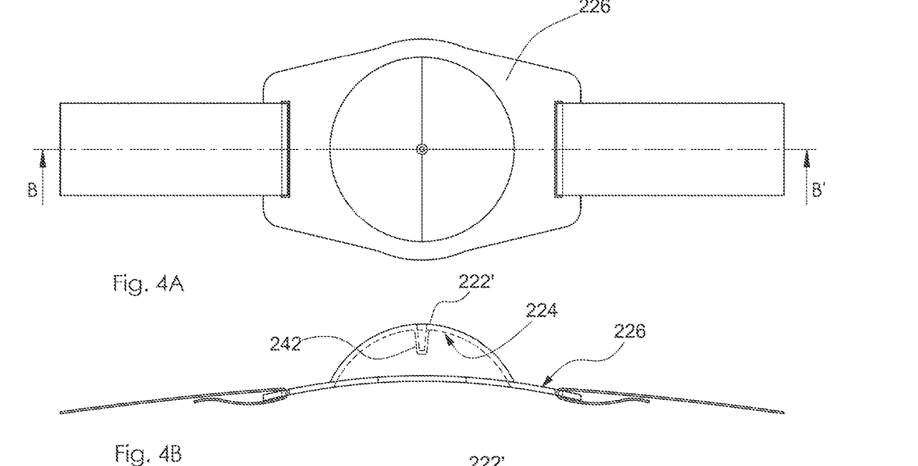
FIG. 4A is a top plan view of the example device of FIG. 4.
FIG. 4B is a side elevation view of the example device of FIG. 4.
Figure 4C:
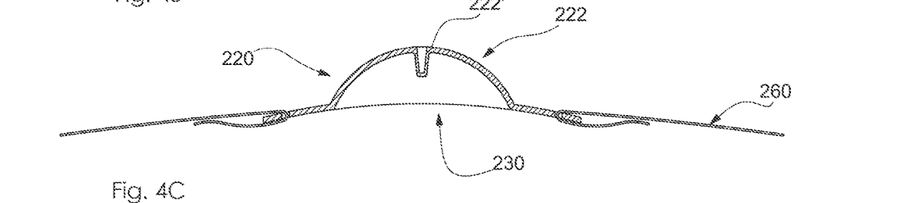
FIG. 4C is a cross-sectional view of the example device of FIG. 4 taken along a longitudinal section line which passes through the longitudinal centerline B-B' of the device of FIG. 4A.
Figure 4D:
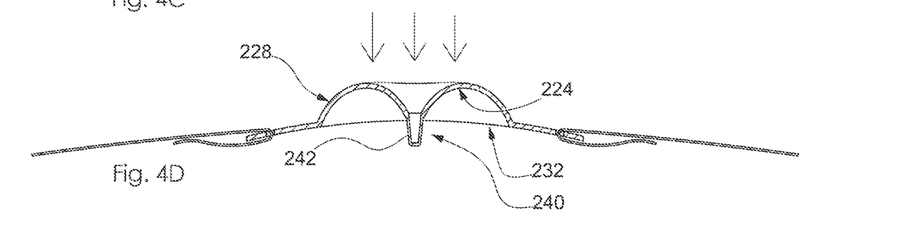
FIG. 4D is the cross-sectional view of FIG. 4C with the example device deformed in response to an axially applied compressive force.

An example sitting posture alert device 200 comprises a cross-leg detector 220 and an alert device 240, as depicted in FIG. 4. This alert device 200 is substantially identical to the alert apparatus 100 except that the thigh sensing structure comprises a dome-shaped thigh sensing body without spaced-apart stays. In other words, the spaced stays of the alert device 100 are replaced by an umbrella-shaped top member having a closed top rather than a top member having apertures defined by stays. The description on and in relation to the alert device is incorporated herein by reference mutatis mutandis with numerals increased by 100 where appropriate or where the context permits.

For example, while the top member of the alert device 200 is no longer defined by the plurality of spaced apart stays, the top member defines a closed sensing assembly and cooperate with the base member 226 to define a dome shaped or partially spherical shaped structure or assembly having a dome shaped or partially spherical shaped hollow or substantially hollow internal space or compartment. In this embodiment, the umbrella-shaped top member and the dome-shaped sensing assembly is resiliently deformable and operates in a similar manner to that of the stay-defined sensing assembly of the alert apparatus 100.

In some embodiments, the alert device 120, 220 may be detachable from the attachment means. In some embodiments, the attachment means may include a suction device, such as a suction cup, so that a user does not need to wear a band in order to attach the alert device on the user body. In some embodiments, the attachment means is formed on the base portion, for example, integrally formed on the base portion 126, 226. For example, self-adhesive substances may be applied on the underside of the base portion 126, 226 to make the base portion 120, 220 also function as a self-attaching attachment device.

In both embodiments, when the dome-shaped sensing assembly is deformed from the neutral, or extended, state to the deformed, or retracted, state, the ceiling changes from a dome-shaped top into a depressed top having a depressed compartment surrounded by the deformed stays or the peripheral portion surrounding the main sensing surface.

In typical uses, a user may wear the alert apparatus 100, 200 with the base member in contact abutment with the wearing thigh and the main thigh sensing surface offset from the surface in contact with the base portion. When in this wearing configuration, the main thigh sensing surface is elevated from and facing away the wearing thigh, the free end of the protruding member 142, 242 faces towards the wearing thigh, and the wearing thigh will receive the alert signal when crossed leg sitting occurs.

In alternative uses, a user may wear the alert apparatus 100, 200 with the main thigh sensing surface in abutment contact with the wearing thigh and with the free end of the protruding member 142, 242 projecting away from the wearing thigh. When in this wearing configuration, the approaching thigh will receive the alert signal when crossed leg sitting occurs.

Figure 5:
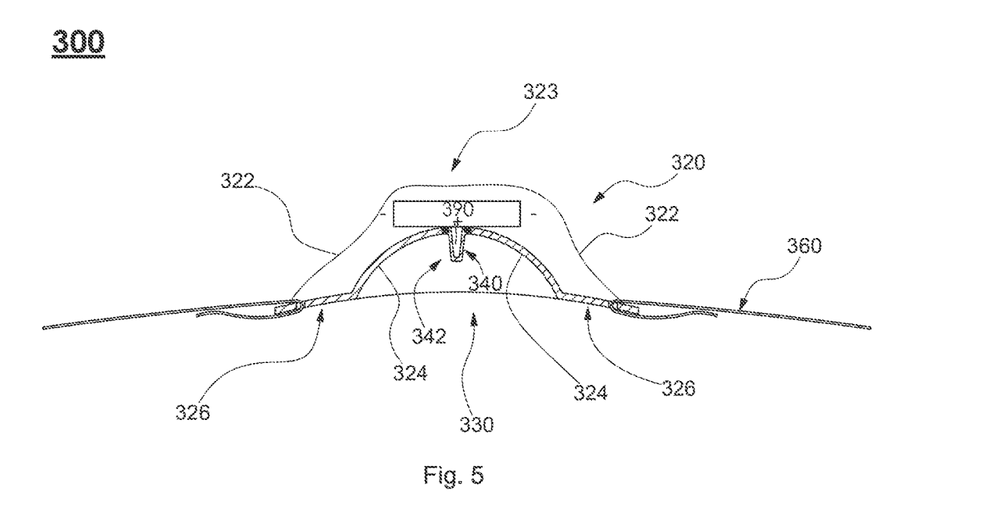
FIG. 5 is a schematic cross-sectional view of an example crossed-leg alert device.

An example alert apparatus 300 depicted in FIG. 5 comprises an alert device 320 mounted on an attachment band 360. The alert device 320 comprises a crossed leg detector and an alert generator 340. The crossed leg detector comprises a main body having a first surface 322, a second surface 324, a base portion 326 and a base aperture 330 defined by the base portion. A central portion 323 is defined on the top portion of the main body. In this example, the central portion 323, the base aperture 330 and the base portion share a common central axis and the common central axis is orthogonal or substantially orthogonal to a contact plane defined by the base portion 326. The first and second surfaces are axially elevated from the base portion 326 by a hollow support structure, the axial direction being parallel to the shared central axis. The first and second surfaces, the hollow support structure and the base portion cooperate to define a hollow structure having a hollow internal compartment. The hollow support structure is a resilient structure which provides resilient support to the central portion to elevate the central port 323 axially away from the base portion 326. The hollow support structure is resiliently deformable and the central portion is movable between a neutral, detection or standby state and an activation state. When the central portion 323 is at the neutral state, the neutral states is furthest away from the base portion. When the central portion is at the activation or deformed state, the central portion 323 is moved closer to the base portion 326. When crossed leg situation is not present, an urging force due to inherent resilience of the support structure will urge the central portion to return to the neutral state.

Figure 5A:
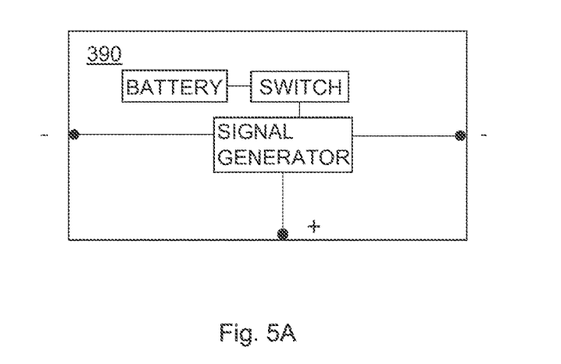
FIG. 5A is a block diagram of an electronic component of the crossed-leg alert device of FIG. 5.

The alert generator 340 comprises an alert circuit 390 and an alert electrode 342. The alert circuit 390 is embedded inside the main body and between the first and second surfaces. The alert electrode 342 projects from the second side of the main body and extends axially towards the base aperture of the base portion. The alert circuit 390 has a first output (+) which is connected to the base portion 326 and a second output (−) which is connected to the alert electrode 342, the alert electrode being a contact electrode. The alert circuit 390 is for generating an alerting signal to a user when activated, and comprises a batter, a shock signal generator, and a switch. The switch is operable in a standby state and an activation state. When in the standby state, no electric alert signal is generated at the alert electrode. When in the activation state, a non-hazardous yet human perceivable electric alert signal is generated. When the switch is in the activation state, the base portion 326, the alert electrode 342, the alert circuit 390 and the user form a complete electric circuit through which an electric alert signal will flow. The electric alert signal to be generated by the alert circuit 390 is a non-hazardous electric alert signal which is perceivable by a user. For example, the alert signal may be in the form of shock pulses at a medium to low voltage (say 12-50 volt) and at a very low current level (<10 uA) lasting for several seconds. The central portion 323 of the main body which is intermediate the first and the second surfaces and inside which the alert circuit 390 is housed is deformable and will be compressively deformed when thighs of a wearer are crossed with the central portion 323 under compression of the crossed thighs. When the central portion 323 is compressively deformed, the built-in switch is activated so that the alert signals will flow through the skin of the wearer.

To provide a switchable signal flow path, both the alert electrode 342 and the base portion 326 are electrically conductive while the alert electrode 342 and the base portion 326 are electrically insulated from each other unless and until the switch is activated. In some embodiments, the contact electrode 342 is formed as a stud member having the same description as that of the embodiment of FIG. 1. In some embodiments such as the present, both the contact electrode 342 and the base portion 326 are moulded of a conductive material such as carbonized rubber and electrical insulation is provided between the contact electrode 342 and the base portion 326 when in the neutral state.

In use, the alert apparatus 300 is worn on a thigh of a user in the same manner of that as depicted in FIG. 3C. When crossed leg occurs, compressive force due to leg crossing will bring about activation of the alert circuit 390 whereby an electrical alert signal is generated and will flow through skin of the wearer. When activation deformation occurs, the contact electrode 342 will be in abutment contact with the skin and the length of the contact electrode 342 can be adjusted so that a physical pressure is applied on the portion of the wearer skin surrounded by the base portion 326, similar to the action of the stud member 142. Therefore, in this example embodiment, both electrical and physical alert signals are generated and applied to the wearer when crossed leg posture is detected by the first surface, which functions as an incoming thigh detection surface. In some embodiments, the length of the contact electrode 342 is arranged so that no or minimal physical pressure is felt by the wearer when the alert device 320 is deformed due to crossed leg posture.

Apart from the alert circuit 390, a thickened central portion 323 for receiving the alert circuit 390 and the possible dual functionalities of the contact electrode 342 to operate also as a pressure applicator, the structure, operation and description of the alert device 320 are substantially identical to that of the alert device 120 and the apparatus 100, the description herein on and in relation to the alert device 120 and the apparatus 100 is incorporated herein by reference mutatis mutandis with numerals increased by 200 where the context permits or is appropriate.

Figure 6A:
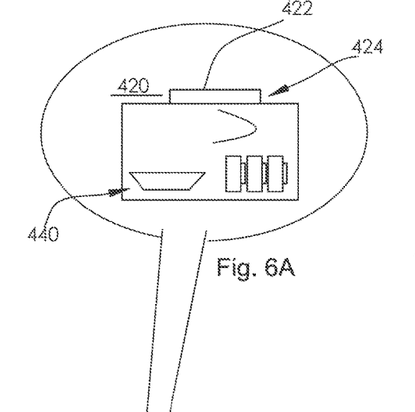
FIG. 6A is a schematic view depicting another example cross-leg alert device.
Figures 6A, 6B, 6B:
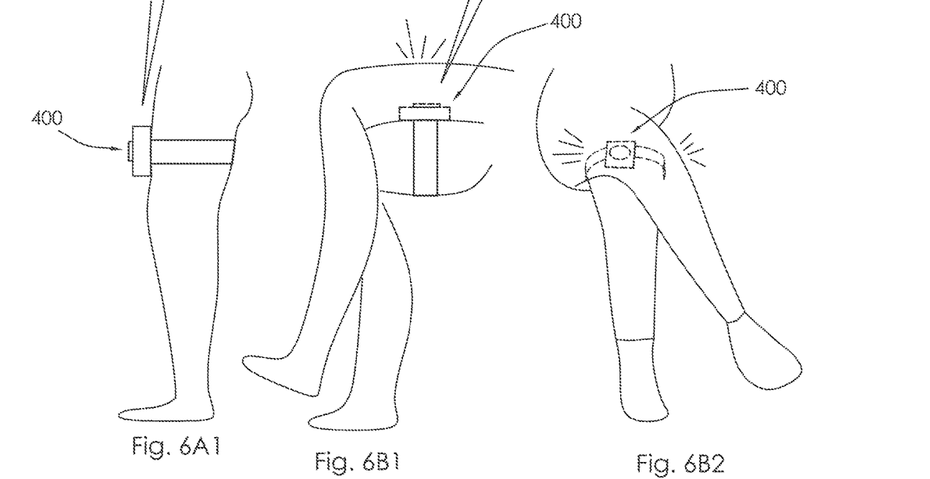
Figure 6B:
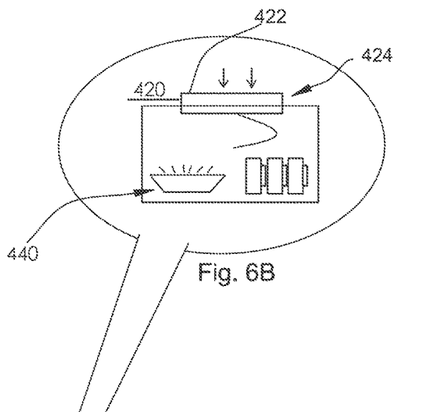
FIG. 6B depicts an example operation state of the example cross-leg alert device of FIG. 6A when cross-legged sitting is detected.

An example sitting posture alert apparatus 400 comprises a cross-leg detector or alert device 420 and an alert generator 440, as depicted schematically in FIG. 6A. The alert device 400 is mounted on an attachment means such as a wearing band similar to that described above. The alert device 440 comprises a base member having a device casing inside which electronic alert circuitry for generating an alert is housed. The alert circuitry comprises an alert circuit which is powered by batteries and generates a buzzing sound when actuated. The alert circuit is actuatable by an actuator 424 which is mounted on the device casing and movable in an axial direction relative to the device casing between a neutral or an un-actuated state of FIG. 5A and a depressed or actuated state of FIG. 5B. A main sensing surface 422 is defined on the actuator 424, for example, on a top or free surface at the free end of the actuator 424 distal form the device casing.

The alert device is worn on the thigh of a user for detection of contact abutment with an approaching thigh and to generate an alert upon detection of a change in sitting posture from non-cross-legged to cross legged sitting.

In use, a user may wear the alert device 400 with the base member or the actuator in contact abutment with the wearing thigh and the alert circuitry will generate an alert when cross legged sitting that would trigger or activate the alert circuitry occurs. The alert may be in the form of buzzing sound, for example, high frequency buzzing sound, vibrations, non-hazardous electric shock, other alert signals, or their combination and the circuitry are appropriately devised without loss of generality.

In some embodiments, the alert generator is a signal generator, generating signal to be received by an external device such as mobile or computer. Apart from alerting the user to change the sitting posture, the signal could be used to calculate the time of leg crossing to track the progress of removing the habit of leg-crossing.

Figure 7A:
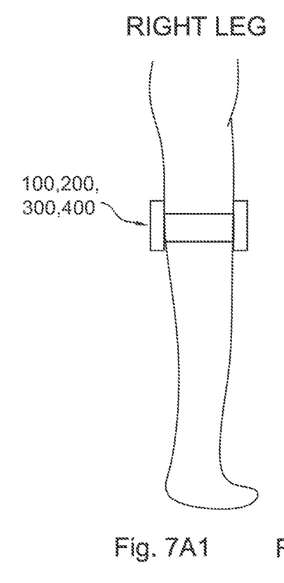
Figures 7A, 7B:
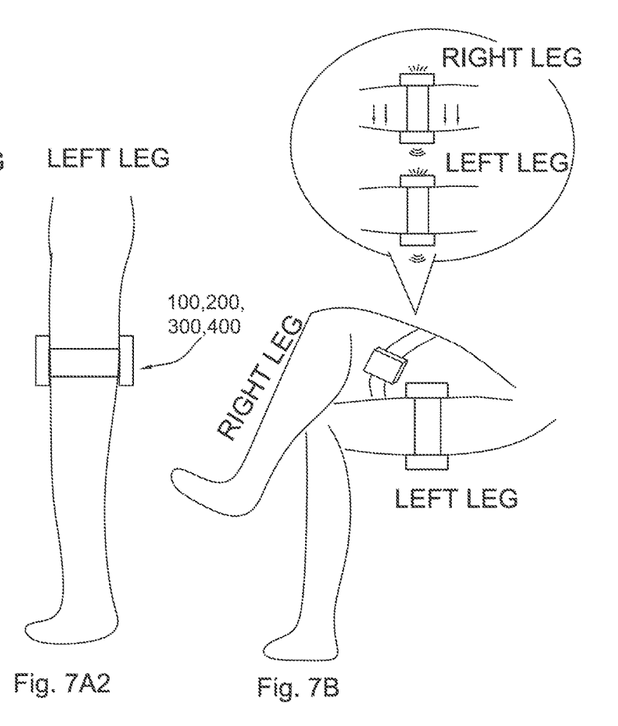

In some embodiments, a plurality of alert apparatus 100, 200, 300, 400 is included to form a cross-leg alert apparatus, as depicted in FIGS. 7A1 and 7A2 where two alert devices are attached to a wearing band. For example, alert devices 100, 200, 300, 400 may be disposed on a wearing band at diametrically opposite locations when worn to cater for both types of cross-legged sitting postures, that is, left-on-right or right-on-left. The alert devices on the same apparatus may be of the same or different types without loss of generality.

Figure 8:
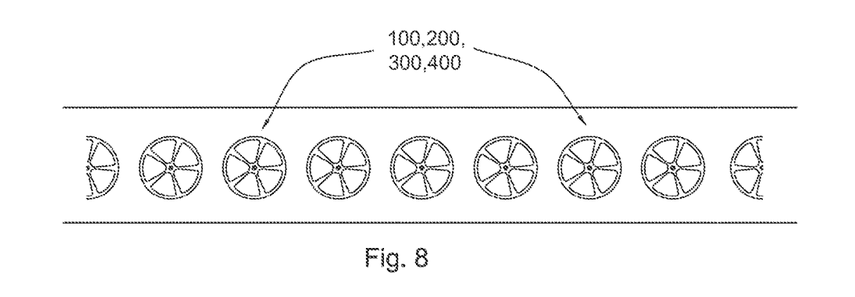
FIG. 8 is a plan view of another example cross-leg alert apparatus.

In some embodiments, a plurality of alert devices may be arranged to distribute in a direction that is at an angle that is not orthogonal to the length of the thigh to cater for possible change in positions of contact abutment between the wearing leg and the approaching leg, as depicted in FIG. 8. For example, a plurality of alert devices may be distributed along the length of the thigh whether parallel to the axis of the thigh or helically.

While the disclosure has been made with reference to the examples herein, it should be understood that the examples are for reference and should not be used for restricting the scope of disclosure.

Table of numerals

| | | | |
|---|---|---|---|
| 100 | Alert device | 128, 122' | thigh sensing sub-assembly, aka incoming thigh sensing sub-assembly |
| 120 | cross-leg detector 120 | | |
| 122 | first surface, aka incoming-thigh detection surface, thigh sensing surface and incoming-thigh sensing surface | | |
| | | 140 | alert generator 140 |
| | | 142 | Stud member |
| | | 160 | thigh attachment device |
| 122' | main thigh sensing surface 122' | | |
| 123 | Central portion | | |
| 124 | second surface 124, aka under side of main body | | |
| 126 | Base portion | | |
| 128 | stay | | |
| 129 | Inter-stay aperture | | |
| 130 | Main aperture, aka base aperture | | |

The invention claimed is:

1. An alert device for wearing on a thigh of a user, the alert device comprising an alert generator, wherein the alert generator comprises an alert signal generation device for generating a user perceivable alert signal when the user is in a crossed leg sitting posture when both thighs of the user are in abutment contact with the alert device and with the alert device between both thighs.

2. The alert device according to claim 1, wherein the alert signal is in the form of an applied pressure, the applied pressure being at a harmless level which is sufficient to cause perception or notice of the user; a non-harmful and user perceivable electric shock or pulse; or an audible sound.

3. The alert device according to claim 1, wherein the alert generator comprises a pressure applicator which is arranged to generate a harmless but perceivable or noticeable pressure on thigh skin of the user or pain during alert operations; an electric shock generator which is arranged to generate a harmless but noticeable electric shock or shock pulses to the user during alert operations; or an audible generator which is arranged to generate an audible alarm to the user during alert operations.

4. The alert device according to claim 1, further comprising a second thigh detector, wherein the second thigh detector is to function as an incoming thigh detector for detecting an incoming thigh and comprises a second thigh detection surface, and the second thigh detection surface is movable between a detection state or standby state when no alert signal is generated to the user by the alert generator and an activation state when the alert signal is generated to the user by the alert generator; and wherein the second thigh detection surface is arranged to trigger, activate or operate the alert generator to generate the alert signal when crossed leg sitting of the user is detected by the second thigh detector.

5. The alert device according to claim 4, wherein the alert device comprises a base portion which is in abutment contact with a wearing thigh of a user when the alert device is worn on the wearing thigh and defines a thigh contact surface, and wherein the second thigh detector or the second thigh detection surface is axially elevated or offset from the base portion by a resiliently deformable support structure and is to move in an axial direction to change its axial levels when moving between the standby or detection state and the activation state.

6. The alert device according to claim 5, wherein the second thigh detection surface, the support structure and the base portion cooperate to define a resiliently deformable hollow structure and the hollow structure defines a hollow internal compartment, and wherein the alert generator is inside the hollow internal compartment at least when in the standby or detection state.

7. The alert device according to claim 5, wherein the second thigh detection surface, the support structure and the base portion are integrally formed from a semi-rigid, resilient and mouldable material.

8. The alert device according to claim 5, wherein the second thigh detector comprises a central portion and the second thigh detection surface faces away from the base portion, and an under-surface which is on opposite side of and is opposite facing to the second thigh detection surface, and wherein the alert generator comprising a stud member which is suspended from the central portion and extends towards the base aperture in the axial direction.

9. The alert device according to claim 8, wherein the central portion and the base portion share a common central axis, the common axis being orthogonal to both the central portion and the base portion.

10. The alert device according to claim 8, wherein the support structure comprises a plurality of spaced part stays and an inter-stay aperture is defined between adjacent stays, and wherein the stays extend radially from the central portion and curves concavely to join the base portion to form a dome-shaped hollow support structure when in the standby or detection state.

11. The alert device according to claim 10, wherein the dome-shaped hollow support structure is to become a double arched shaped hollow support structure when changed from the standby or detection state to the activation state.

12. The alert device according to claim 4, wherein the alert device comprises a resilient biasing device which is arranged to bias the second thigh detection surface in the standby or detection state and to provide an urging force to return the thigh detection surface to the standby or detection state when in the activation state.

13. The alert device according to claim 4, wherein the alert device is for wearing on a stationary thigh and the second thigh detection surface is an incoming thigh detection surface for detecting an incoming thigh which moves towards abutment contact with the stationary thigh to form a crossed leg sitting posture; or wherein the alert device is for wearing on a moving thigh and the second thigh detection surface is stationary thigh detection surface for detecting a stationary thigh which is in abutment contact with the moving thigh to form a crossed leg sitting posture.

14. The alert device according to claim 1, wherein the alert generator comprises electrical or electronic circuitry to generate audible or skin sensible or perceivable alert signals and a switch operable to actuate the electrical or electronic circuitry to generate the audible or skin sensible or perceivable alert signals.

15. The alert device according to claim 14, wherein the switch is operable between an actuation state to actuate the electrical or electronic circuitry to generate an alert signal and a standby state when the electrical or electronic circuitry does not generate an alert signal; and wherein the thigh detection surface forms part of the switch so that movement of the thigh detection surface from the standby or detection position to the actuation position is to move the switch from the standby or detection state to the actuation state.

16. The alert device according to claim 1, wherein the alert signal generation device is a weight-actuated alert signal generator.

17. A cross-leg alert apparatus comprising an alert device for wearing on a thigh of a user, the alert device comprising an alert generator, wherein the alert generator comprises an alert signal generation device for generating a user perceivable alert signal when the user is in a crossed leg sitting posture when both thighs of the user are in abutment contact with the alert device and with the alert device between both thighs; and an attachment means for attaching the alert device to a first thigh of a user.

18. The cross-leg alert apparatus according to claim 17, wherein the attachment means is a resilient or elastic band and the alert device is mounted on the resilient or elastic band; or wherein the attachment means comprises a self-adhesive device integrally formed on a base portion of the alert device.

19. The cross-leg alert apparatus according to claim 17 and comprises a plurality of alert devices, wherein the alert devices are distributed along length of the apparatus.

* * * * *